(12) United States Patent
Yang et al.

(10) Patent No.: US 11,357,478 B2
(45) Date of Patent: Jun. 14, 2022

(54) METHODS AND SYSTEMS FOR SHEAR WAVE ELASTOGRAPHY

(71) Applicant: Massachusetts Institute of Technology, Cambridge, MA (US)

(72) Inventors: Heng Yang, Cambridge, MA (US); Brian W. Anthony, Cambridge, MA (US); Felix Jan van de Donk, Eindhoven (NL)

(73) Assignee: Massachusetts Institute of Technology, Cambridge, MA (US)

( * ) Notice: Subject to any disclaimer, the term of this patent is extended or adjusted under 35 U.S.C. 154(b) by 152 days.

(21) Appl. No.: 16/604,811

(22) PCT Filed: Apr. 11, 2018

(86) PCT No.: PCT/US2018/027113
§ 371 (c)(1),
(2) Date: Oct. 11, 2019

(87) PCT Pub. No.: WO2018/191381
PCT Pub. Date: Oct. 18, 2018

(65) Prior Publication Data
US 2021/0196234 A1     Jul. 1, 2021

Related U.S. Application Data

(60) Provisional application No. 62/483,994, filed on Apr. 11, 2017.

(51) Int. Cl.
*A61B 8/00* (2006.01)
*A61B 8/08* (2006.01)
(Continued)

(52) U.S. Cl.
CPC ............ *A61B 8/485* (2013.01); *A61B 8/4209* (2013.01); *A61B 8/429* (2013.01); *A61B 8/4245* (2013.01);
(Continued)

(58) Field of Classification Search
CPC ......... A61B 8/485; A61B 8/54; A61B 8/4494; A61B 8/429; A61B 8/4245; A61B 8/4209; A61B 5/0048; G01S 15/8918; B06B 1/045
See application file for complete search history.

(56) References Cited

U.S. PATENT DOCUMENTS 7,859,144 B1    12/2010  Sahyoun
9,339,256 B2    5/2016   Specht et al.
(Continued)

OTHER PUBLICATIONS

Mellema, Daniel C. et al., "Probe Oscillation Shear Elastography (PROSE): A High Frame-Rate Method for Two-Dimensional Ultrasound Shear Wave Elastography", IEEE Transactions of Medical Imaging, vol. 35, No. 9 Sep. 2016 , 9 Pages.
(Continued)

*Primary Examiner* — Christopher Koharski
*Assistant Examiner* — Taylor Deutsch
(74) *Attorney, Agent, or Firm* — Strategic Patents, P.C.

(57) ABSTRACT

A mechanical vibration source for a shear wave elastography system has a contact surface shaped to provide a point source of mechanical energy when striking a target surface of a medium. This point source usefully mitigates high frequency components and other artifacts in an induced shear wave. Other techniques may be used in combination with this mechanical energy source to improve shear wave elastography and facilitate miniaturization for deployment, e.g., within a handheld imaging device.

18 Claims, 6 Drawing Sheets

(51) Int. Cl.
  B06B 1/04 (2006.01)
  G01S 15/89 (2006.01)
(52) U.S. Cl.
  CPC .............. A61B 8/4494 (2013.01); A61B 8/54 (2013.01); B06B 1/045 (2013.01); G01S 15/8918 (2013.01)

(56) References Cited

U.S. PATENT DOCUMENTS

| | | | |
|---|---|---|---|
| 2008/0200805 | A1 | 8/2008 | Hoyt et al. |
| 2010/0168586 | A1* | 7/2010 | Hillman ............... G02B 26/101 600/476 |
| 2011/0063950 | A1 | 3/2011 | Greenleaf et al. |
| 2011/0152690 | A1 | 6/2011 | Anthony et al. |
| 2012/0008929 | A1 | 1/2012 | David et al. |
| 2012/0083692 | A1* | 4/2012 | Stoll ....................... A61B 8/429 600/437 |
| 2014/0180091 | A1 | 6/2014 | Mcaleavey |
| 2014/0330122 | A1 | 11/2014 | Baghani et al. |
| 2017/0020486 | A1 | 1/2017 | Salcudean et al. |

OTHER PUBLICATIONS

Yamakoshi, Yoshiki et al., "Ultrasonic Imaging of Internal Vibration of Soft Tissue under Forced Vibration", IEEE Transactions on Ultrasonics, Ferroelectrics, and Frequency Control. vol. 37. No. 2 Mar. 1990 , 9 Pages.

Sandrin, Laurent et al., "Shear Elasticity Probe for Soft Tissues with 1-D Transient Elastography", IEE Transactions on Ultrasonics, Ferroelectrics, and Frequency Control, vol. 49, No. 4 Apr. 2002 , 11 Pages.

Sandrin, Laurent et al., "Shear Modulus Imaging with 2-D Transient Elastography", IEEE Transactions on Ultrasonics, Ferroelectrics, and Frequency Control, vol. 49, No. 4 Apr. 2002 , 10 Pages.

WIPO, "PCT Application No. PCT/US18/27113 International Preliminary Report on Patentability dated Oct. 24, 2019", 14 pages.

ISA, "PCT Application No. PCT/US18/27113 International Search Report and Written Opinion dated Jul. 12, 2018", 21 pages.

* cited by examiner

METHODS AND SYSTEMS FOR SHEAR WAVE ELASTOGRAPHY

CROSS-REFERENCE TO RELATED APPLICATIONS

This application is a national stage entry application of International Patent Application No. PCT/US18/27113 filed on Apr. 11, 2018, which claims priority to U.S. Provisional Application No. 62/483,994 filed on Apr. 11, 2017, where the entire contents of each of the foregoing are hereby incorporated by reference.

FIELD OF THE INVENTION

The invention generally relates to shear wave elastography, and more particularly to shear wave elastography techniques using external mechanical vibration sources to induce shear waves in a medium.

BACKGROUND

Shear wave elastography (SWE) has emerged as a useful diagnostic tool for evaluating tissue elasticity. Existing clinical SWE imaging devices typically rely on complex and expensive acoustic radiation force (ARF) systems to generate shear waves. While various techniques have been demonstrated for external, mechanical alternatives, these efforts have yet to yield a practical SWE imaging system suitable for deployment with a handheld ultrasound imaging probe. There remains a need for improved SWE imaging devices.

SUMMARY

A mechanical vibration source for a shear wave elastography system has a contact surface shaped to provide a point source of mechanical energy when striking a target surface of a medium. This point source usefully mitigates high frequency components and other artifacts in an externally, mechanically induced shear wave. Other techniques may be used in combination with this mechanical energy source to improve shear wave elastography and facilitate miniaturization for deployment, e.g., within a handheld imaging device In one aspect, an apparatus disclosed herein may include an ultrasound imaging device including a linear ultrasound imaging array with a contact surface for placing against a target surface of a medium to capture an interior image of the medium, a point source of mechanical energy coupled to the ultrasound imaging device, the point source including a second contact surface shaped to initially contact the target surface at a single point when directed toward the target surface over a range of orientations including a normal to the target surface, a driver configured to mechanically drive the point source of mechanical energy along an axis within the range of orientations from a location off the target surface into the target surface of the medium to create a shear wave, and a controller configured to capture ultrasound images from the ultrasound imaging device while operating the driver to create the shear wave.

In another aspect, an apparatus disclosed herein may include an imaging device for capturing an interior image of a medium, a point source of mechanical energy coupled to the imaging device, the point source including a contact surface for contacting a surface of the medium to create a shear wave through the medium when the imaging device is placed for use to capture the interior image, a driver configured to mechanically drive the point source of mechanical energy into the surface of the medium to create the shear wave, and a controller configured to operate the imaging device and the driver in cooperation to capture the interior image while creating the shear wave when the imaging device is placed for use to capture the interior image.

The contact surface of the point source may form a partial sphere for contacting the surface of the medium. The contact surface of the point source may be radially symmetric about an axis through the contact surface and include no high frequency spatial components. The contact surface of the point source may include a convex surface shaped to provide initial contact with the medium at a single point. The contact surface may include a curved shape selected to mitigate high frequency components within the shear wave. The driver may be configured to drive the contact surface of the point source into the surface of the medium along an axis substantially normal to the surface of the medium. The apparatus may further include two or more point sources. The two or more point sources may be positioned in line with a line through a linear ultrasound array of the imaging device. The two or more point sources may be positioned transverse to a line through a linear ultrasound array of the imaging device. The controller may be configured to operate the two or more point sources to steer the shear wave toward a region of interest within the medium. The apparatus may further include a strain relief configured to separate the point source from a surface of the medium when the imaging device is placed for use on the surface of the medium. The apparatus may further include a strain relief to physically enforce an offset between the point source and a surface of the medium when the imaging device is positioned for use in contact with the surface of the medium. The imaging device may include a linear ultrasound array, where the apparatus may further include a second contact surface of the linear ultrasound array for placing in contact with a surface of the medium, and a strain relief extending from the imaging device and defining a line between a location where the strain relief contacts the surface of the medium when the imaging device is placed for use and a second location on the second contact surface of the linear ultrasound array, where an extremity of the point source is offset from the line away from the medium when the imaging device is placed for use and the driver is prepared to mechanically drive the point source of mechanical energy into the surface of the medium to create the shear wave. The driver may include a voice coil actuator to linearly drive the point source toward the surface of the medium. The driver may include a Hall effect sensor configured to detect a position of the point source. The driver may include a free floating cylindrical magnet positioned within a conductive coil and controllable by a current through the conductive coil to accelerate toward the surface of the medium and impact a stop within the conductive coil to deliver kinetic energy through the point source and create the shear wave. The imaging device may be a linear ultrasound array. The imaging device may capture images of a transverse plane through the medium using acoustic energy that propagates through the medium at least one order of magnitude more quickly than the shear wave generated by the driver and the point source. The point source may be positioned relative to the imaging device so that the point source has an offset from a surface of the medium when the imaging device is placed for use against the surface of the medium, where the driver is configured to drive the point source through the offset into contact with the surface in order to strike the surface and create the shear wave. The imaging device may include a force-controlled ultrasound probe configured to apply a predetermined contact force to the surface of the medium while in use.

In one aspect, a method disclosed herein may include positioning a point source of mechanical energy near a surface of a medium, driving the point source into contact with the surface of the medium to create a shear wave through the medium, and capturing an image of a transverse plane through the medium intersecting with the shear wave as the shear wave travels through the medium.

Positioning the point source near the surface may include positioning the point source between about 0.5 millimeters and about 2 millimeters from the surface. The method may further include positioning a second point source of mechanical energy near the surface of the medium and driving the second point source into the surface to create a second shear wave coordinated with the shear wave to create a magnitude peak within a region of interest in the medium. Driving the point source may include driving the point source with an intermittent sinusoidal wave having a frequency of between 30 Hz and 100 Hz. Driving the point source may include driving the point source with an intermittent sinusoidal wave having a frequency of between 40 Hz and 60 Hz. Driving the point source may include driving the point source with an intermittent sinusoidal wave having a frequency that propagates as a shear wave through human soft tissue at between about three to about five meters per second. Capturing the image may include capturing the image with an acoustic imaging device that applies sound at a frequency that propagates through human soft tissue at least one order of magnitude more quickly than the shear wave created by driving the point source into the surface of the medium. Capturing the image may include capturing the image with an ultrasound array. Capturing the image may include applying a predetermined contact force to the surface of the medium while capturing the image.

BRIEF DESCRIPTION OF THE FIGURES

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

DETAILED DESCRIPTION

Embodiments will now be described with reference to the accompanying figures. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. The words "about," "approximately" or the like, when accompanying a numerical value, are to be construed as indicating any deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. The use of any and all examples or exemplary language ("e.g.," "such as," or the like) is intended merely to better illuminate the embodiments and does not pose a limitation on the scope of the disclosed embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms unless expressly stated otherwise.

Figure 1:
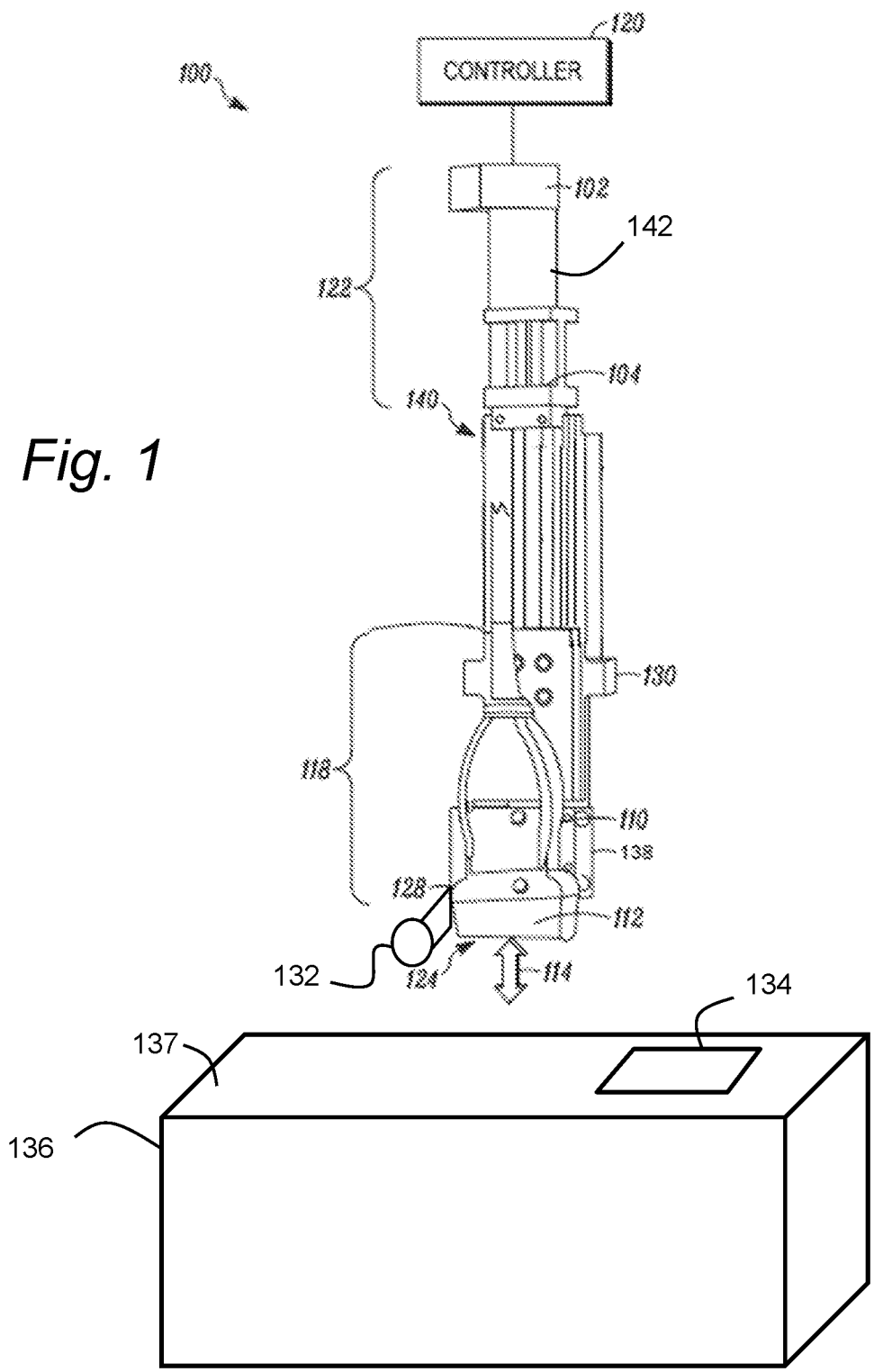
FIG. 1 is a perspective view of a handheld ultrasound probe control device.

FIG. 1 is a perspective view of a handheld ultrasound probe control device. The device 100 may include a frame 118 adapted to receive a probe 112, a linear drive system 122 that translates the frame 118 along an actuation axis 114, a sensor 110 such as a force sensor, a torque sensor, position sensor 142 or some combination of these, and a controller 120. In general, this device 100 described below may be used to measure and control an instantaneous contact force while capturing ultrasound images, and may be usefully combined with the shear wave elastography techniques contemplated herein, e.g., to monitor or control tissue strain within an imaging medium or to control the manner in which a mechanical vibration source engages with a surface of the imaging medium.

The probe 112 can be of any known type or construction. The probe 112 may, for example include a handheld ultrasound probe used for medical imaging or the like. More generally, the probe 112 may include any contact scanner or other device that can be employed in a manner that benefits from the systems and methods described herein. Thus, one advantage of the device 100 is that a standard off-the-shelf ultrasound medical probe can be retrofitted for use as a force-controlled ultrasound in a relatively inexpensive way; i.e., by mounting the probe 112 in the frame 118. Medical ultrasound devices come in a variety of shapes and sizes, and the frame 118 and other components may be adapted for a particular size/shape of probe 112, or may be adapted to accommodate a varying sizes and/or shapes. In another aspect, the probe 112 may be integrated into the frame 118 or otherwise permanently affixed to or in the frame 118.

In general, a probe 112 such as an ultrasound probe includes an ultrasound transducer 124. The construction of suitable ultrasound transducers is generally well known, and a detailed description is not required here. In one aspect, an ultrasound transducer includes piezoelectric crystals or similar means to generate ultrasound waves and/or detect incident ultrasound. More generally, any suitable arrangement for transmitting and/or receiving ultrasound may be used as the ultrasound transducer 124 such as a linear ultrasound imaging array or any other arrangement of ultrasound transducers or other imaging sensors. Still more generally, other transceiving mechanisms or transducers may also or instead be used to support imaging modalities other than ultrasound. Thus, the probe 112 may include any of a variety of imaging devices suitable for capturing subsurface images of tissue while shear waves are propagating therethrough.

The frame 118 may include any substantially rigid structure that receives and holds the probe 112 in a fixed position and orientation relative to the frame 118. The frame 118 may include an opening that allows an ultrasound transducer 124 of the probe 112 to contact a patient's skin or other surface through which ultrasound images are to be obtained. Although FIG. 1 shows the probe 112 held within the frame 118 between two plates (a front plate 128 bolted to a larger plate 130 on the frame 118) arranged to surround a handheld ultrasound probe and securely affix the probe to the frame 118, the frame 118 may more generally include any structure or combination of structures suitable for retaining the probe 112 in a fixed position.

In one aspect, the frame 118 may be adapted for handheld use, and more particularly adapted for gripping by a technician in the same orientation as a conventional ultrasound probe. Without limitation, this may include a trunk 140 or the like that extends axially away from the ultrasound transducer 124 and generally normal to the contact surface of the transducer 124, or substantially parallel to the actuation axis 114, and be shaped and sized for gripping by a human hand. In this manner, the trunk 140 may be gripped by a user in the same manner and orientation as a typical handheld ultrasound probe. The linear drive system 122 may advantageously be axially aligned with the trunk 140 to permit a more compact design consistent with handheld use. That is, a ballscrew or similar linear actuator may be aligned to pass through the trunk 140 without diminishing or otherwise adversely affecting the range of linear actuation.

The linear drive system 122 may be mounted on the device 100 and may include a control input electronically coupled to the controller 120. The linear drive system 122 may be configured to translate the probe 112 along an actuation axis 114 in response to a control signal from the controller 120 to the control input of the linear drive system 122. Additionally, the linear drive system 122 may include a position sensor 142 to provide position information characterizing a position of the probe 112 along the actuation axis 114. The position may, for example, be a position relative to one or more travel limits of the linear drive system 122. Although the linear drive system 122 is depicted by way of example as a motor 102 and a linear actuator 104, any system capable of linearly moving the probe 112 can be employed. For example, the linear drive system 122 can include a mechanical actuator, hydraulic actuator, pneumatic actuator, piezoelectric actuator, electro-mechanical actuator, linear motor, telescoping linear actuator, ballscrew-driven linear actuator, and so on. More generally, any actuator or combination of actuators suitable for use within a grippable, handheld form factor such as the trunk 140 may be suitably employed as the linear drive system 122. In some implementations, the linear drive system 122 is configured to have a low backlash (e.g., less than 3 µm) or no backlash in order to improve positional accuracy and repeatability.

The ability of the probe 112 to travel along the actuation axis 114 permits the technician some flexibility in hand placement while using the device 100. In some implementations, the probe 112 can travel up to six centimeters along the actuation axis 114, although greater or lesser ranges of travel may be readily accommodated with suitable modifications to the linear actuator 104 and other components of the device 100.

The motor 102 may be electrically coupled to the controller 120 and mechanically coupled in a fixed positional relationship to the linear actuator 104. The motor 102 may be configured to drive the linear actuator 104 in response to control signals from the controller 120, as described more fully below. The motor 102 can include a servo motor, a DC stepper motor, a hydraulic pump, a pneumatic pump, and so on.

The sensor 110, which may include a force sensor and/or a torque sensor, may be mechanically coupled to the frame 118, such as in a fixed positional relationship to the frame 118 in order to sense forces/torques applied to the frame 118, e.g., by the probe 112. The sensor 110 may also be electronically coupled to the controller 120, and configured to sense a contact force between the probe 112 and a target surface (also referred to herein simply as a "target") such as a body from which ultrasound images are to be captured. As depicted, the sensor 110 may be positioned between the probe 112 and the back plate of the frame 118. Other deployments of the sensor 110 are possible, so long as the sensor 110 is capable of detecting the contact force (for a force sensor) between the probe 112 and the target surface. Embodiments of the sensor 110 may also or instead include a multi-axis force/torque sensor, a plurality of separate force and/or torque sensors, or the like.

The sensor 110, which may include the force sensor, may be mechanically coupled to the ultrasound probe 112 and configured to determine or provide a signal indicative of a force applied by the ultrasound probe 112 to the surface of a target 136 such as skin over human tissue. The force sensor may include a pressure transducer coupled to the ultrasound probe 112 and configured to sense an instantaneous contact force between the handheld ultrasound probe 112 and the skin.

The sensor 110 can provide output in any known form, and may generally provide a signal indicative of forces and/or torques applied to the sensor 110. For example, the sensor 110 can produce analog output such as a voltage or current proportional to the force or torque detected. Alternatively, the sensor 110 may produce digital output indicative of the force or torque detected. Moreover, digital-to-analog or analog-to-digital converters (not shown) can be deployed at any point between the sensors and other components to convert between these modes. Similarly, the sensor 110 may provide radio signals (e.g., for wireless configurations), optical signals, or any other suitable output that can characterize forces and/or torques for use in the device 100 described herein.

The controller 120 generally includes processing circuitry to control operation of the device 100 as described herein. The controller 120 may receive signals from the sensor 110 indicative of force/torque and from the position sensor 142 of the linear drive system 122 indicative of the position of the probe 112 relative to the travel end points, and may generate a control signal to a control input of the linear drive system 122 (or directly to the linear actuator 104) for maintaining a given contact force between the ultrasound probe 112 and the target 136, as described more fully below. The controller 120 may include analog or digital circuitry, computer program code stored in a non-transitory computer-readable storage medium, and so on. Embodiments of the controller 120 may employ pure force control, impedance control, contact force-determined position control, and so on.

The controller 120 may be configured with preset limits relating to operational parameters such as force, torque, velocity, acceleration, position, current, etc. so as to immediately cut power from the linear drive system 122 when any of these operational parameters exceed the preset limits. In some implementations, these preset limits are determined based on the fragility of the target 136. For example, one set of preset limits may be selected where the target 136 is a healthy human abdomen, another set of preset limits may be selected where the target 136 is a human abdomen of an appendicitis patient, etc. In addition, preset limits for operational parameters may be adjusted to accommodate discontinuities such as initial surface contact or termination of an ultrasound scan (by breaking contact with a target surface).

Other sensors (indicated generically as a second sensor 138) may be included without departing from the scope of this invention. For example, a second sensor 138 such as an orientation sensor or the like may be included, which may be operable to independently detect at least one of a position and an orientation of the device 100, such as to track location and/or orientation of the device 100 before, during, and after use. This data may help to further characterize operation of the device 100. A second sensor 138 such as a range or proximity detector may be employed to anticipate an approaching contact surface and place the device 100 in a state to begin an ultrasound scan and/or shear wave generation. For example, a proximity sensor may be operable to detect a proximity of the ultrasound transducer 124 to a subject (e.g., the target surface). One or more inertial sensors may also or instead be used to anticipate or detect contact with a measurement surface such as accelerometers and gyroscopes, or any other device or combination of devices that measure motion. More generally, any of a variety of sensors known in the art may be used to augment or supplement operation of the device 100 as contemplated herein.

The device 100 may further include a sensor for illuminating the skin surface when the handheld ultrasound probe is placed for use against the skin surface. For example, the sensor may be a lighting source mechanically coupled to the handheld ultrasound probe and positioned to illuminate the skin surface during use of the ultrasound probe. The lighting source may be part of the sensor system of the ultrasound probe or the lighting source may be a separate device directed toward the ultrasound probe. Suitable lighting sources include an LED light or any other light capable of illuminating the skin surface during ultrasound scanning.

The device 100 may include a shear wave generation system 132 such as an external mechanical vibration source or the like. In general, the shear wave generation system 132 is used to create shear waves within the target 136 that can be imaged using the device 100 and used to estimate tissue elasticity for diagnostic or other purposes. The shear wave generation system 132 may, for example, include a contact-based source of mechanical energy that can be applied to the target 136 and used to controllably apply shear waves, e.g., while contact force is controlled and images are being captured by the device 100. The shear wave generation system 132 is described in further detail herein.

The ultrasound probe 112 may be used to capture an ultrasound image of a target 136 through a skin surface 137. A fiducial marker 134 with predetermined dimensions may be applied to the skin surface 137 of the target 136 that is to be scanned by the ultrasound probe 112. The fiducial marker 134 may have any desired dimension or shape such as a square, a rectangle, a circle and/or any other regular, irregular, and/or random shape and/or patterns, and may generally be employed to assist in orientation to an imaging target or recovery of a prior acquisition state. In one embodiment, the fiducial marker 134 may be a 3 mm×3 mm square. The fiducial marker 134 may be made of a thin material. Suitable materials include, but are not limited to, any materials that will not obstruct the transducer from obtaining an ultrasound scan of the target 136. The fiducial marker 134 may be adhered to the skin surface 137 of a target 136 using any suitable methods and/or any suitable adhesives. In another aspect, the fiducial marker 134 may be stamped, inked or otherwise applied to the skin surface using ink or any other suitable, visually identifiable marking material(s).

Figure 2:
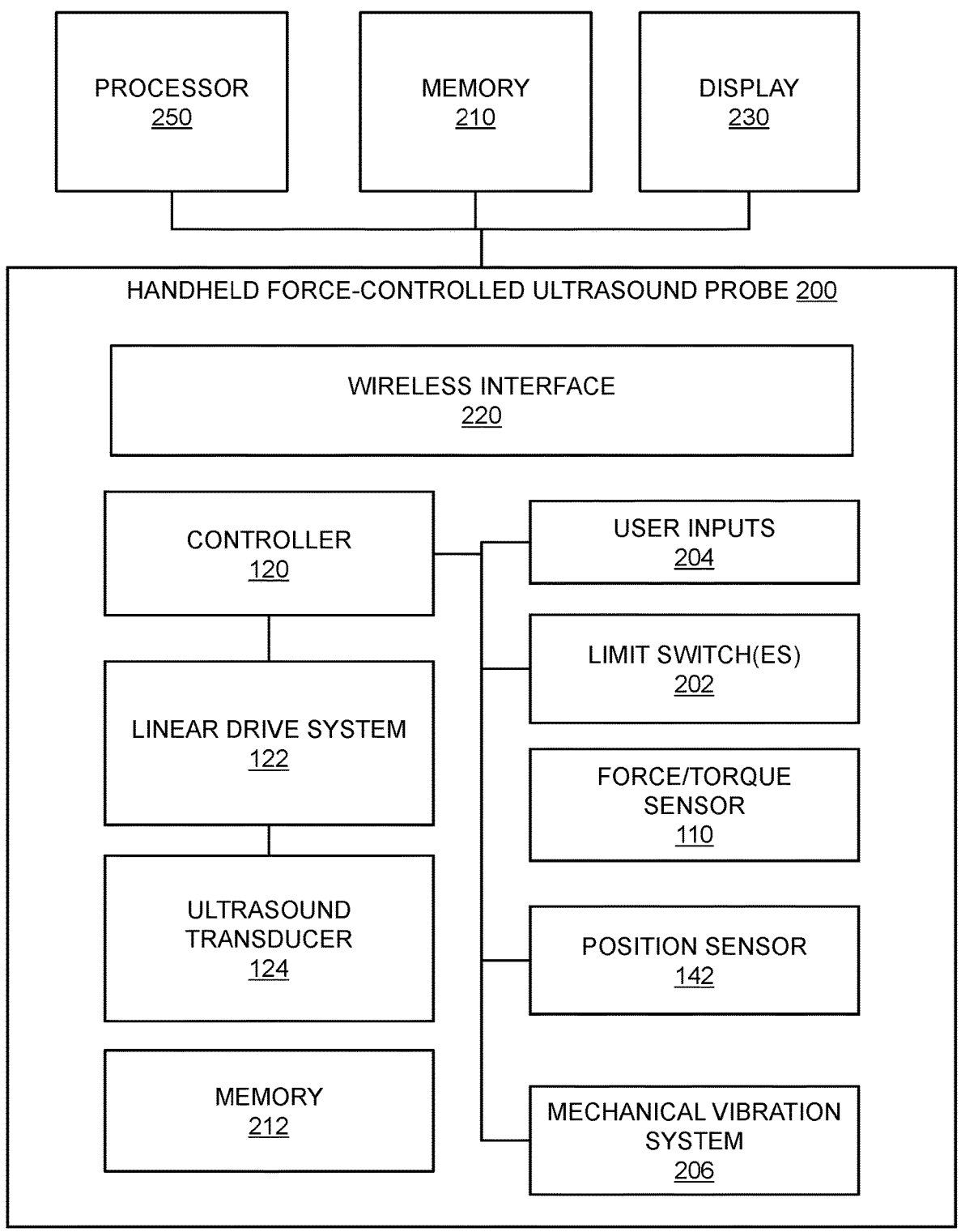
FIG. 2 is a schematic view of a handheld ultrasound probe.

FIG. 2 is a schematic depiction of a handheld force-controlled ultrasound probe. The probe 200, which may be a force-controlled ultrasound probe, generally includes a sensor 110, a controller 120, a linear drive system 122, position sensor 142, an ultrasound transducer 124, and a mechanical vibration system 206, all as described herein.

The probe 200 may have a sensor 110, controller 120, and linear drive system 122, such as any of the corresponding components described herein, which may be integrally mounted in a single device to provide a probe 200 with an integral structure. In FIG. 2, the components are all operable to gather ultrasound images at measured and/or controlled forces and torques, as described above with reference to FIG. 1. In embodiments, the various functions of the above-described components may be distributed across several independent devices in various ways (e.g., an ultrasound probe with integrated force/torque sensors but external drive system, an ultrasound probe with an internal drive system but external control system, etc.). In one aspect, a wireless handheld probe 200 may include a wireless interface 220 that transmits sensor data and/or ultrasound data wirelessly to a remote computer that captures data for subsequent analysis and display.

The ultrasound transducer 124 can include any suitable ultrasound transducer or transducer array including, without limitation, a medical ultrasonic transducer or an industrial ultrasonic transducer. Other inputs/sensors may be usefully included in the probe 200. For example, the probe 200 may include a limit switch 202 or multiple limit switches 202 to provide positioning information to the controller 120 concerning physical limits for linear travel of the linear drive system 122. A position sensor 142 including the limit switch(es) 202 or independent of the limit switch(es) may provide information concerning a position of the linear drive system 122 (or a component coupled to the linear drive system 122). The probe 200 may also or instead include one or more user inputs 204 such as buttons, switches, dials and the like for receiving user inputs to control operation of the probe 200. A memory 210 may be provided to store ultrasound data from the ultrasound transducer and/or sensor data acquired from any of the sensors during an ultrasound scan. Another memory 212 may also store such data on the probe 200, as well as program instructions or the like for controlling operation of the probe 200.

The probe 200 may include a mechanical vibration system such as the shear wave generation system described above, or any other system for externally applying mechanical energy to create and propagate a shear wave in a target medium of interest.

A display 230 may be provided, which may receive wired or wireless data from the probe 200. The display 230 and memory 210 may be a display and memory of a desktop computer or the like, or may be standalone accessories to the probe 200, or may be integrated into a medical imaging device that includes the probe 200, memory 210, display 230 and any other suitable hardware, processor(s), and the like. The display 230 may display ultrasound images obtained from the probe 200 using known techniques. The display 230 may also or instead display a current contact force or instantaneous contact force measured by the sensor 110, which may be superimposed on a corresponding ultrasound image or in another display region of the display 230. Other useful information, such as a target contact force, an actuator displacement, or an operating mode, may also or instead be usefully rendered on the display 230 to assist a user in obtaining ultrasound images. The display 230 may also display shear wave images, tissue elasticity, or other shear wave elastography information useful for examination or diagnostic purposes.

A processor 250 may also be provided. In one aspect, the processor 250, memory 210, and display 230 are a desktop or laptop computer. In another aspect, these components may be separate, or some combination of these. For example, the display 230 may be a supplemental display provided for use by a doctor or technician during an ultrasound scan. The memory 210 may be a network-attached storage device or the like that logs ultrasound images and other acquisition state data. The processor 250 may be a local or remote computer provided for post-scan or in-scan processing of data. In general, the processor 250 and/or a related computing device may have sufficient processing capability to perform the processing contemplated herein. For example, the processor 250 may be configured to process an image of a subject from the ultrasound transducer 124 of the probe 200 to provide an estimated image of the subject at a predetermined contact force of the ultrasound transducer. This may, for example, be an estimate of the image at zero Newtons (no applied force), or an estimate of the image at some positive value (e.g., one Newton) selected to normalize a plurality of images from the ultrasound transducer 124. In another aspect, the processor 250 may be configured to process data from the probe 200 to support shear wave elastography imaging as contemplated herein.

Figure 3:
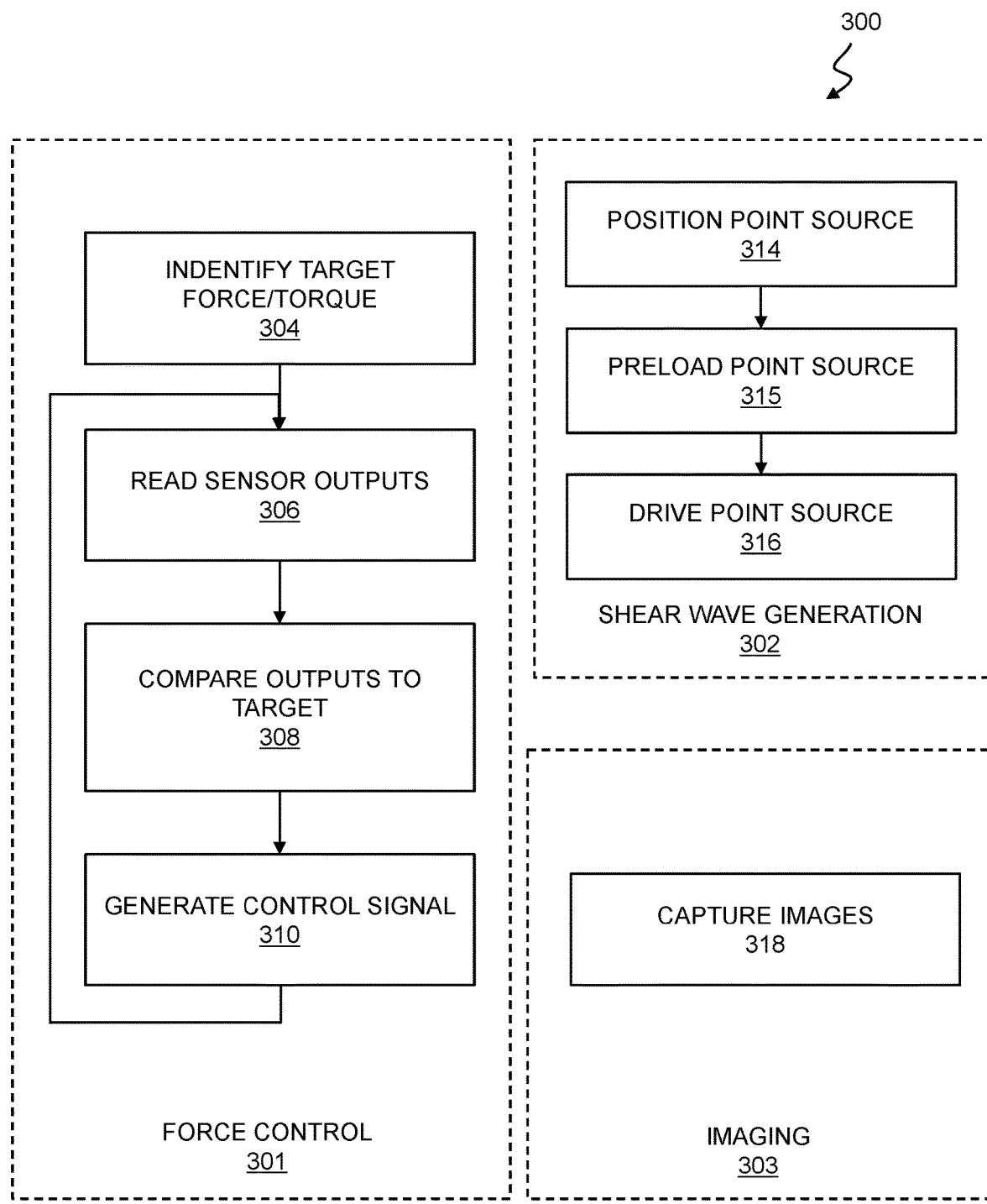
FIG. 3 is a flowchart of a process for force-controlled acquisition of ultrasound images.

FIG. 3 is a flowchart of a process for force-controlled acquisition of ultrasound shear wave elastography images. The process 300 can be performed, e.g., using any of the probes described herein. The process 300 is generally divided into three sub-processes, a force control process 301, a shear wave generation process 302, and an imaging process 303, each of which may be concurrently, sequentially, or otherwise controlled or coordinated, e.g., by a controller or processor, to support shear wave elastography imaging as contemplated herein.

As shown in step 304, the process 300 may include identifying target force and/or torque values for a probe. In this step, target imaging conditions can be identified, such as a predetermined or target force for contact between a probe and a target surface, or where appropriate, a target torque. The target force may be a constant force. For example, in imaging a human patient, a constant force of less than or equal to 20 Newtons is often desirable for the comfort and safety of the patient.

The target force may also or instead vary as a function of time. For example, it may be useful to "poke" a target in a controlled manner, and acquire images of the target as it deforms during or after the poke. The desired force may also or instead include a desired limit (minimum or maximum) for manually applied force. In some implementations, the desired force may include a gradual increase and decrease, or any other pattern suitable for capturing images as contemplated herein. In another aspect, a desired force function may involve increasing the applied force by some function F(t) for a specified time period until satisfactory imaging, patient comfort, or a combination of these is achieved, and maintaining that force thereafter until completion of a scan. The above functions are given by way of example. In general, any predetermined force function can be used.

As shown in step 306, the process 300 may include reading sensor outputs, such as the output from force, torque, and position sensors. These outputs may be read as inputs to a controller or the like and used to control operation of a linear actuator or the like to provide force-controlled imaging.

As shown in step 308, the process 300 may include comparing sensor outputs to the target value(s) to determine a force differential. In some implementations, the comparison can be accomplished by computing an absolute measure such as the difference of the sensor output with the corresponding desired sensor output. Similarly, a relative measure such as a ratio of output to the desired output can be computed. Additionally, output from the position sensor 142 may be compared to the positions of the limit switch(es) 202 to determine if the probe 200 is approaching an end of travel of the linear drive system 122. Many other functions can also or instead be used.

As shown in step 310, the process may include generating a control signal based on the comparison of actual-to-desired sensor outputs (or, from the perspective of a controller/processor, sensor inputs). The control signal may be such that the linear drive system is activated in such a way as to cause the measured force and/or torque to be brought closer to a desired force and/or torque at a given time. For example, if a difference between the measured force and the desired force is computed, then the drive system can translate the probe with a force whose magnitude is proportional to the difference, and in a direction to reduce or minimize the difference. Similarly, if a ratio of the desired force and measured force is computed, then the drive system can translate the probe with a force whose magnitude is proportional to one minus this ratio.

More generally, any known techniques from control theory or the like can be used to drive the measured force towards the target force (or measured torque to target torque, as appropriate). These techniques include linear control algorithms, proportional-integral-derivative (PID) control algorithms, fuzzy logic control algorithms, and so on. By way of example, the control signal may be damped in a manner that avoids sharp movements of the probe against a patient's body. In another aspect, a closed-loop control system may be adapted to accommodate ordinary variations in a user's hand position. For example, a human hand typically has small positional variations with an oscillating frequency of about four Hertz to about twenty Hertz. As such, the controller may be configured to compensate for an oscillating hand movement of a user at a frequency between four Hertz and thirty Hertz (or any other suitable range), e.g., by providing a time resolution for control that is finer than twenty Hertz or thirty Hertz, preferably at least sixty Hertz or greater, accompanied by an actuation range within the time resolution larger than typical positional variations associated with jitter or tremors in an operator's hand, e.g., of a few millimeters or so.

Before, during, or after controlling force (e.g., using the force control process 301 as generally described above), or any combination of these, the process 300 may include a shear wave generation process 302. It will be understood that shear wave generation may also or instead be used without concurrent force control; however, force control can confer significant advantages such as controlling the force with which a mechanical actuator vibrates against a target surface to create a shear wave, and controlling (e.g., increasing) tissue strain to improve or otherwise control propagation of the shear wave within target tissue.

As shown in step 314, the process 300 may include positioning a point source of mechanical energy for use in creating a shear wave in a medium. This may, for example, include positioning the point source near the surface, at the surface, or pressed into the surface. The medium may, for example, include human tissue and the surface of the medium may be human skin. More generally, the medium may include any medium that might usefully be analyzed using shear wave elastography as contemplated herein.

A variety of useful point sources are described in further detail below. In general, a point source can provide a single, initial point of contact when striking a target surface in order to provide a simple, spherical wavefront for a resulting shear wave. This can be generally achieved using, e.g., smooth, curved surfaces, or other shapes with no sharp edges, corners, discontinuities, or surfaces or contours having high spatial frequency components.

The point source may usefully be positioned, e.g., about 0.5 mm away from the surface, about 1 millimeters away from the surface, about 2 millimeters away from the surface, or between about 0.5 and 2 millimeters away from the surface. More generally, the point source may be positioned at any distance that provides clearance for the drive system to accelerate the point source into the target surface and increase the kinetic energy delivered on impact, particularly for a compact drive system suitable for use with a handheld imaging device. While in some implementations it may be advantageous to position the point source away from the target surface, in certain implementations, the point source may contact the target surface, i.e., the point source may be disposed 0 millimeters from the target surface so that they are in contact. For example, the point source may be preloaded against the target surface. The positioning of the point source may be dependent upon the power capability of the actuator—e.g., if the actuator is powerful enough, then the point source may be in contact with the surface before vibration/activation.

It will be understood that numerous point sources of mechanical energy may be employed. For example, the process 300 may include positioning a second point source of mechanical energy near the surface of the medium and driving the second point source into the surface to create a second shear wave coordinated with the shear wave (a first shear wave) to create a magnitude peak within a region of interest in the medium.

As shown in step 315, the process 300 may include preloading the point source, e.g., with potential energy suitable for driving the point source to create a desired shear wave.

As shown in step 316, the process 300 may include driving the point source. Where the point source is positioned near, but not in contact with, the surface, this may include driving the point source into contact with the surface of the medium to create a shear wave through the medium. In another aspect, the point source may be place in contact and the process 300 may include driving the point source for this or any other suitable starting position relative to the target surface.

A variety of driving strategies may be employed according to, e.g., the properties of the medium being imaged, the region of interest relative to the point source(s), the amount of initial contact force applied by an imaging system, and so forth. Current dynamic elastography techniques use shear wave excitations at frequencies of about 50-400 Hertz. Thus, in one aspect suitable for use with ultrasound imaging of human tissue, driving the point source may include driving the point source with an intermittent sinusoidal wave having a frequency of between about 30 Hz and 100 Hz. In another aspect, driving the point source may include driving the point source with an intermittent sinusoidal wave having a frequency of between about 40 Hz and 60 Hz. In general, shear waves of this frequency range can propagate in human tissue at a velocity on the order of a few meters per second. Ultrasound frequency imaging waves, e.g., from an ultrasound array, may have significantly higher frequencies and propagate at velocities at least an order of magnitude, and potentially several orders of magnitude, greater than the shear wave, which can make it possible to capture moving images of the shear wave propagating through the medium using ultrasound techniques.

As known in the art, it may also be useful to create a shear wave with an intermittent sinusoidal driving force, e.g., with a cycle of a sinusoid followed by a period of inactivity to prevent wave collisions and other imaging artifacts. Thus, in one aspect, driving the point source may include driving the point source with an intermittent sinusoidal wave having a frequency that propagates as a shear wave through human soft tissue at between about three to about five meters per second.

Driving the point source may also or instead include driving a second point source in a manner coordinated with driving the first point source. This may, for example, include driving the second point source in phase with the first point source, slightly out of phase, or substantially out of phase as appropriate to create any desired constructive interference between corresponding shear waves. More generally, a number of point sources may be used in combination, e.g., to create regions of increased shear wave magnitude in regions of interest for imaging.

With the force control process 301 controlling contact force with a target medium, and with the shear wave generation process 302 creating shear waves in the medium, the imaging process 303 may be used to capture images of shear wave propagation through the medium in order to evaluate tissue elasticity and the like.

As shown in step 318, the process 300 may include capturing images. This may, for example, include capturing an image of a transverse plane through the medium intersecting with the shear wave as the shear wave travels through the medium. For example, a linear ultrasound transducer array may capture an image of a transverse plane through the medium in the plane of the array. Thus, this may include capturing an image with an ultrasound array such as a linear ultrasound array, or more generally, with an acoustic imaging device that applies acoustic energy at a frequency that propagates through human soft tissue at least one order of magnitude more quickly than the shear wave created by driving the point source into the surface of the medium. Still more generally, this may include capturing images with any device consistent with the target medium and imaging modality, e.g., with capturing shear wave elastography images in human tissue.

In another aspect, this may include applying a predetermined contact force to the surface of the medium as described above while capturing the image.

The analysis and diagnostic significance of shear wave elastography images, as well as related techniques such as one dimensional transient elastography, point shear wave elastography, and magnetic resonance imaging shear wave elastography are generally known in the art, and are not described here in detail, except to note that shear wave elastography facilitates characterization of tissue elasticity leading to a variety of potentially useful diagnostic results such as assessment of liver fibrosis.

Figure 4:
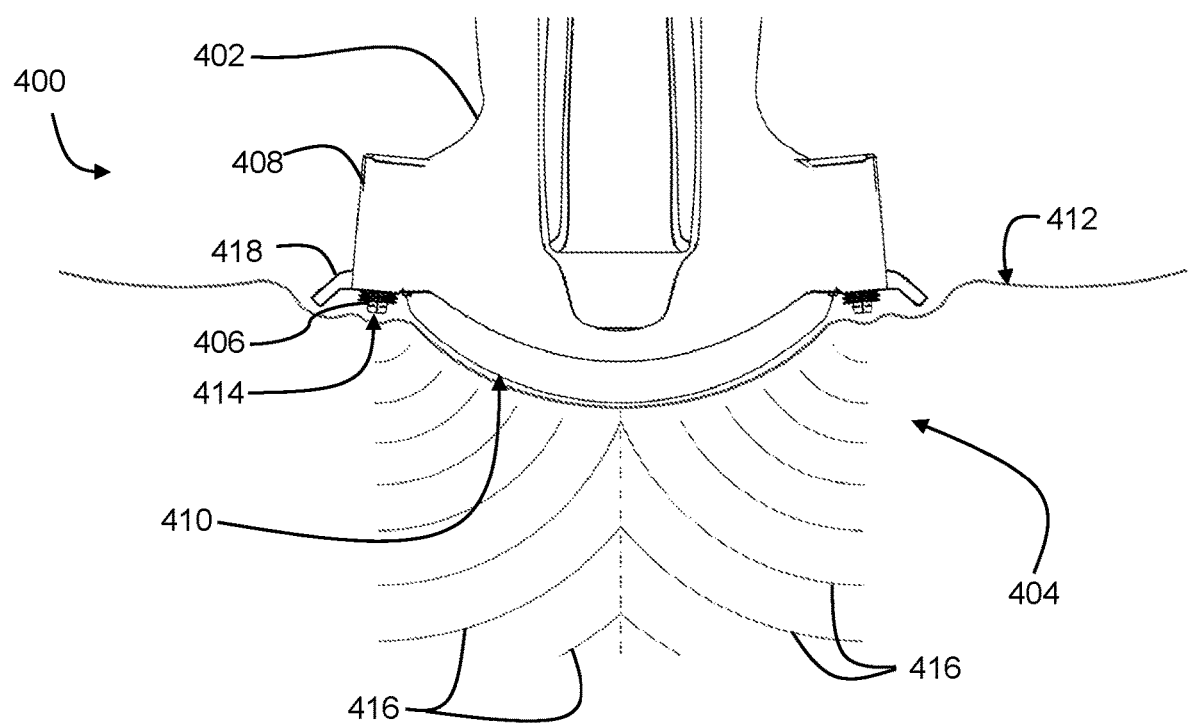
FIG. 4 shows a device for shear wave elastography imaging.

FIG. 4 shows a device for shear wave elastography imaging. In general, the device 400 may include an imaging device 402 for capturing an interior image of a medium 404 such as human tissue, a point source 406 of mechanical energy, a driver 408, and a controller (not shown) such as any of the controllers described herein. The controller may generally be configured to operate the driver 408 to create a shear wave in the medium 404 with the point source 406, or more generally, to operate the imaging device 402 and the driver 408 in cooperation to capture the interior image while creating a shear wave with the driver 408 when the imaging device 402 is placed for use to capture the interior image.

In general, the imaging device 402 may include any imaging device contemplated herein. For example, the imaging device may include an ultrasound imaging device such as an ultrasound imaging transducer, an ultrasound imaging array, or a linear ultrasound imaging array. The imaging device 402 may include a contact surface 410 for placing against a target surface 412 of the medium 404 to capture an interior image of the medium 404. In one aspect, the imaging device 402 may be a force-controlled ultrasound probe configured to apply a predetermined contact force to the surface of the medium 404 while in use, such as any of the force-controlled probes described herein. As described above, in one useful embodiment, the imaging device 402 may capture images of a transverse plane through the medium 404 using acoustic energy that propagates through the medium 404 at least one order of magnitude more quickly than the shear wave generated by the driver 408 and the point source 406.

The point source 406 of mechanical energy may be coupled to the imaging device 402 (e.g., through the driver 408 and related hardware), and may include a contact surface 414 for contacting the target surface 412 of the medium 404 to create a shear wave through the medium 404 when the imaging device 402 is placed for use to capture the interior image and the driver 408 is operated by the controller. One or more of the point sources 406 may be oriented in the transverse plane (in line with the imaging plane) and/or in the sagittal plane (orthogonal to the imaging plane).

The point source 406 may generally be shaped and sized to create a simple or otherwise desirable shear wave in the medium 404 such as a shear wave with a spherical wavefront. To this end, the contact surface 414 of the point source 406 may be shaped to initially contact the target surface at a single point when directed toward the target surface 412 over a range of orientations including normal to the target surface 412. This may exclude, for example, flat or planar surfaces that might be skewed out of alignment with the target surface 412 to create an initial, single point of contact followed by a large, planar impact. The contact surface 414 may more generally include a convex shape with a curved shape selected to mitigate high frequency components within the shear wave. For example, the contact surface 414 may usefully form a partial sphere for contacting the target surface 412, or any other similarly curved, convex shape suitable for creating an initial point contact with the target surface 414. In another aspect, the point source 406 may usefully include a contact surface 414 that is radially symmetric about an axis through the contact surface, e.g., to avoid misshaping the spherical wavefront. In another aspect, the point source 406 may include a contact surface 414 with no high frequency spatial components such as angles, discontinuities, or the like that might create multiple, interfering shear wavefronts within the medium 404.

While physical features such as a smooth curved surface, a radially symmetric curved surface, a spherical surface, and the like may usefully create a substantially spherical wavefront upon impact, it will be understood that any surface that provides an initial point source of contact and does not produce any subsequent interfering waves or interference patterns may usefully be employed as the point source 406 as contemplated herein. In general, this includes a shape that makes an initial point contact along an axis over a range of orientations around a normal to the target surface 412 in order to accommodate a range of orientations of the device 400 to the target surface 412 away from a strict, mathematical normal to the target surface 412. This may generally include a range of orientations consistent with normal operation of an ultrasound imaging device, or otherwise consistent with capture of useful shear wave elastography images from the medium 404.

The driver 408 may be configured to mechanically drive the point source 406 of mechanical energy into the target surface 412 of the medium 404 to create a shear wave, as illustrated by curved lines 416 propagating through the medium 404 in FIG. 4. For a point source 406 that is offset, the driver 408 may more specifically be configured to mechanically drive the point source 406 of mechanical energy from a location off the target surface 412 into the target surface 412 of the medium 404 to create a shear wave. In one aspect, the driver 408 may be configured to drive the contact surface 414 of the point source 406 into the target surface 412 along an axis substantially normal to the surface of the medium 404, e.g., when the device 400 is oriented normal to the target surface 412 for use. More generally, the driver 408 may drive the point source 406 at any suitable orientation, e.g., along an axis within a range of orientations about a normal to the target surface 412, e.g., to follow a corresponding range of possible orientations of the device 400 when placed for use as discussed above.

In general, the driver 408 may include any linear actuator or the like suitable for periodically driving the point source 406 into the target surface 412 as contemplated herein.

In one aspect, the device 400 may include two or more point sources 406. For example, the device 400 of FIG. 4 depicts two point sources 406 positioned in line with a line through a linear ultrasound array of the imaging device 402. That is, the two point sources 406 may be positioned at the respective ends of the linear ultrasound array to create a shear wave interference pattern in a plane intersecting (e.g., substantially normal to) the imaging plane of the array. In another aspect, the two point sources 406 may be positioned transverse to the line through the linear ultrasound array, e.g., to create a shear wave interference pattern in a plane parallel to or within the imaging plane.

The controller may be configured to control operation of the device 400, e.g., by concurrently controlling a force control system, a shear wave generation system, and an ultrasound imaging system as contemplated herein to capture shear wave elastography data. In a device 400 with at least two point sources 406, the controller may be configured to operate the two or more point sources 406 to steer the shear wave toward a region of interest within the medium 404, e.g., by creating a suitable interference pattern between corresponding waves from the point sources 406. To this end, the controller may be configured to operate the two or more point sources 406 to steer the constructive shear wave and/or to control an intensity of the shear wave.

The device 400 may also include a strain relief 418 configured to improve contact between the point source 406 and the target surface 412 as generally described below. For example, the strain relief 418 may be configured to improve the transfer of kinetic energy into the medium 404 by reducing the stiffness of the (local) target surface thus mitigating any impedance mismatch.

Figure 5:
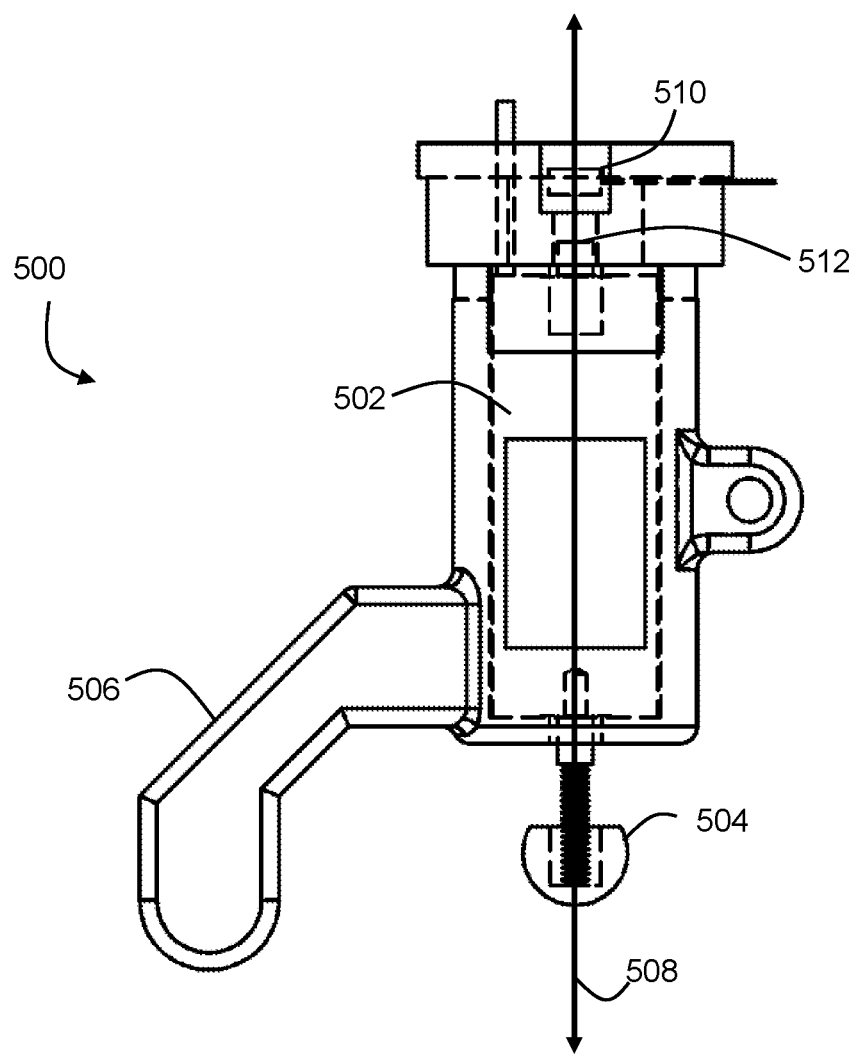
FIG. 5 illustrates a shear wave source.

FIG. 5 illustrates a shear wave source. In general, a shear wave source 500 may include a driver 502, a point source 504 of mechanical energy, and a strain relief 506, which may be any of the drivers, point sources, and strain reliefs described above, and which may be coupled to a device such as any of the imaging devices described above. The shear wave source 500 may also or instead include one or more sensors 510 as described herein.

The driver 502 may include any suitable actuator for generating shear waves as contemplated herein. For example, the driver 502 may include a voice coil actuator having a moving part 512 such as a magnet or the like. Other actuators are also or instead possible. The point source 504 may have a generally curved surface, or as depicted, a substantially spherical surface, or any other contours shaped to form an initial point contact with a target surface when moved toward the target surface along an axis 508 of the driver 502.

The strain relief 506 may be configured to separate the point source 504 from a surface of the medium when the imaging device is placed for use on the surface of a medium such as any of those described herein. In one aspect, the strain relief 506 may more specifically enforce an offset between the point source 504 and a surface of the medium when the imaging device is positioned for use in contact with the surface of the medium. The strain relief 506 may also or instead be used for impedance matching—e.g., to improve the transfer of kinetic energy into the medium by reducing the stiffness of the (local) target surface thus mitigating any impedance mismatch. More generally, the strain relief 506 may be shaped and sized to maintain a separation between the point source 504 and a target surface so that the point source 504 can be accelerated through free space into the target surface in order to increase the kinetic energy delivered on impact. This offset may advantageously facilitate substantial miniaturization of the driver 502 so that the shear wave source 500 can be deployed in a handheld imaging device.

The sensor 510 may include, e.g., a Hall effect sensor or the like. In general, one or more sensors 510 included in the shear wave source 500 may include any sensor suitable for tracking a position or another property, parameter, or characteristic of the shear wave source 500 (i.e., one or more of its components) and/or the target surface. For example, the sensor 510 may be used for closed loop control of position during use. In this manner, in certain implementations, the sensor 510 may sense one or more positions of the moving part 512 of the driver 502 so that a feedback control loop can be formed.

Figure 6:
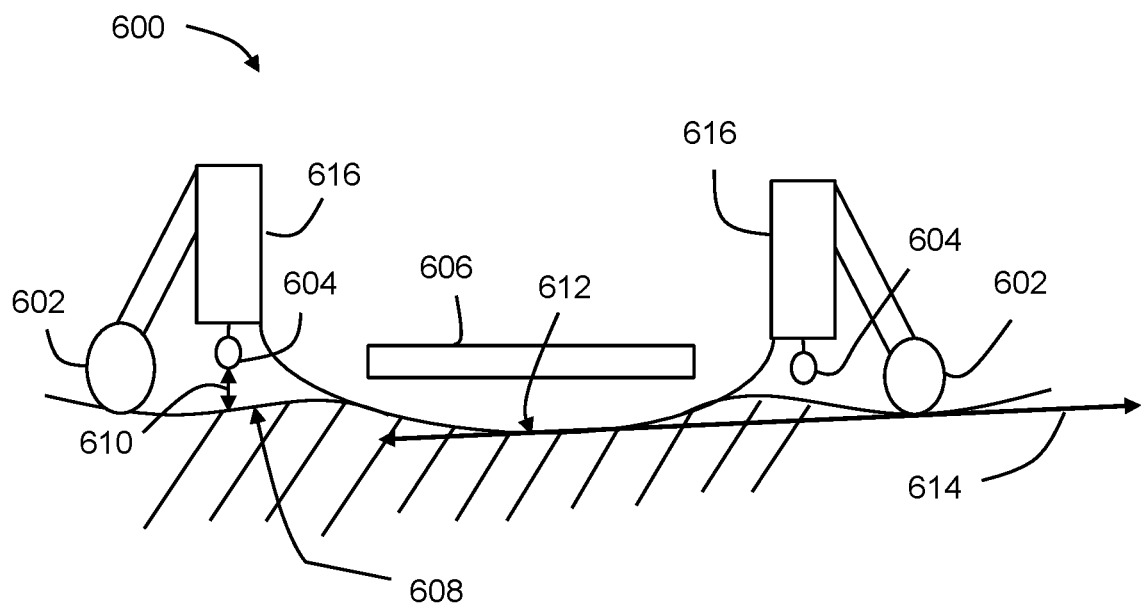
FIG. 6 shows an imaging device with two strain reliefs.

FIG. 6 shows an imaging device with two strain reliefs. In general, the imaging device 600 may include any of the imaging devices described herein. This may, for example, include a linear ultrasound array 606. Unless stated otherwise, for the purposes of this disclosure, a linear ultrasound array 606 is intended to include a linear transducer array in which individual transducers lie in a straight line, as well as a curved transducer array in which individual transducers are arranged in an arc that lies in the imaging plane of the imaging device 600.

In an embodiment, the imaging device 600 may include two strain reliefs 602 positioned about two point sources 604 of mechanical energy. The point source 604 may, for example, lie in, or parallel to, the imaging plane (in the plane of the figure), or the two point sources 604 may be positioned on opposing sides of a plane containing the linear ultrasound array 606 (e.g., above and below the plane of the figure).

In general, the two strain reliefs 602 may enforce an offset 610 between a target surface 608 of the medium being imaged and the point source 604 of mechanical energy. When a contact surface 612 of the linear ultrasound array 606 is placed in contact with the target surface 608 of the medium, the strain reliefs 602 may extend from the imaging device 600 and define a line 614 between a location where the strain relief 602 contacts the target surface 608 and a second location on the contact surface 612 of the linear ultrasound array 606, with an extremity of the point source 604 offset from the line 614 away from the target surface 608 of the medium when the imaging device is placed for use as shown in FIG. 6, and the driver 616 is prepared to mechanically drive the point source 604 of mechanical energy into the target surface 608 of the medium to create a shear wave as generally described herein.

More generally, with or without a strain relief 602, the point source 604 (and the driver 616) may be positioned relative to the imaging device 600 so that the point source 604 has an offset 610 from a target surface 608 of a medium when the imaging device 600 is placed for use against the target surface 608 of the medium. In this configuration, the driver 616 may be further configured to drive the point source 604 through the offset 610 into contact with the target surface 608 in order to strike the target surface 608 and create the shear wave.

Figure 7:
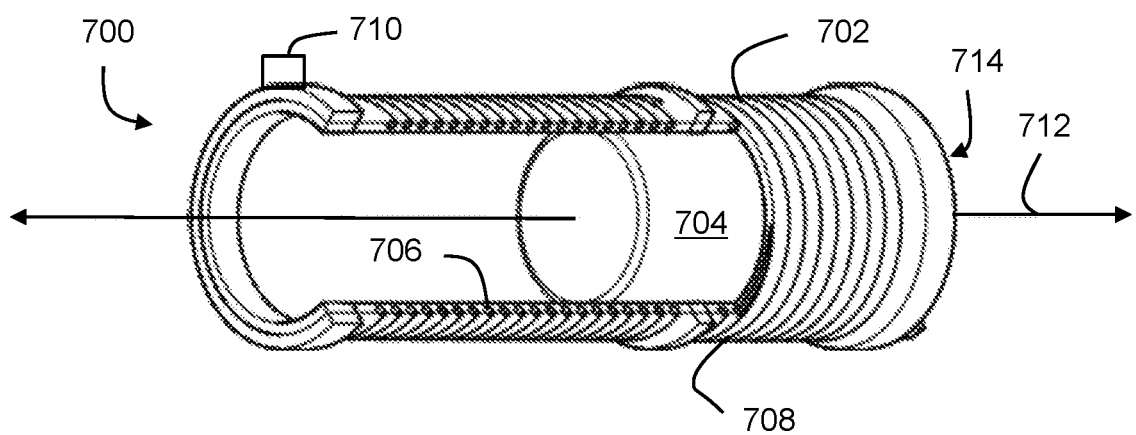
FIG. 7 illustrates a voice coil actuator that may be used as a driver for creating shear waves.

FIG. 7 illustrates a voice coil actuator that may be used as a driver for creating shear waves. The driver 700 may, for example, include a voice coil actuator to linearly drive a point source toward the surface of a medium as generally contemplated herein. In general, the driver 700 may include a frame 702, a magnet 704, a first coil 706, a second coil 708, and a sensor 710.

The frame 702 may be formed of plastic or any other material or combination of materials suitable for imparting the desired mechanical structure without impeding electromagnetic operation of components of the driver 700.

The magnet 704 may be a free floating cylindrical magnet positioned within a conductive coil such as the first coil 706. The magnet 704 may be coupled to a point source (not shown) such as any of the point sources described herein. In general, a position of the magnet 704 along an axis 712 of travel may be controlled by a current through the conductive coil to accelerate toward a surface of a medium and impact a stop 714 within the conductive coil to deliver kinetic energy through the point source and create a shear wave.

The first coil 706 may be wound in the frame about the magnet 704 and a cylinder along the axis 712 of travel, and may be coupled to a current source or the like to drive the magnet 704 toward the stop 714 to deliver kinetic energy for a shear wave. The first coil 706 may thus provide a driving force to drive a point source into contact with a target surface.

The second coil 708 may be wound in the frame about the cylinder formed along the axis 712 of travel at an opposing end of the frame 702 to the first coil 706. The second coil 708 may be operable to reset the magnet 704, e.g., by driving the magnet 704 away from the stop 714 in preparation for a new stroke, and/or retaining the magnet 704 in the ready position until a new cycle is initiated by the first coil 706. The second coil 708 may thus provide a reset force to move the magnet 704 into a ready position for use, e.g., with a point source offset from a target surface.

The sensor 710 may be a Hall effect sensor or any other sensor suitable for tracking a position of the magnet 704 for closed loop control of position during use. In general, the driver 700 should provide for linear travel of the magnet 704, and more particularly for a point source or other fixture coupled to the magnet 704, sufficient to traverse an offset as described above, and further to travel into a target surface a sufficient amount to propagate a shear wave, e.g., about 0.5 millimeters or more into the target surface after traversing the offset.

While the driver 700 may usefully be formed of a voice coil such as that depicted in FIG. 7, it will be understood that any other electromechanical system suitable for delivering kinetic energy to create a shear wave in a target medium, particularly with a handheld probe configuration, may also or instead be used as a driver for an imaging device as contemplated herein.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random-access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. An apparatus comprising:
an ultrasound imaging device including a linear ultrasound imaging array with a contact surface for placing against a target surface of a medium to capture an interior image of the medium;
a point source of mechanical energy coupled to the ultrasound imaging device, the point source including a second contact surface shaped to initially contact the target surface at a single point when directed toward the target surface over a range of orientations including a normal to the target surface;
a driver configured to mechanically drive the point source of mechanical energy along an axis within the range of orientations from a location off the target surface to a location on the target surface of the medium to create a shear wave;
a strain relief configured to contact the target surface of the medium and configured to physically enforce an offset between the target surface of the medium and the location of the point source off the target surface of the medium when the ultrasound imaging device is positioned for use in contact with the medium; and
a controller configured to capture ultrasound images from the ultrasound imaging device while operating the driver to create the shear wave.

2. An apparatus comprising:
an imaging device for capturing an interior image of a medium;
a point source of mechanical energy coupled to the imaging device, the point source including a contact surface for contacting a target surface of the medium to create a shear wave through the medium when the imaging device is placed for use to capture the interior image;
a driver configured to mechanically drive the point source of mechanical energy from a location off the target surface to a location on the target surface of the medium to create the shear wave;
a strain relief configured to contact the target surface of the medium and configured to physically enforce an offset between the target surface of the medium and the location of the point source off the target surface of the medium when the imaging device is positioned for use in contact with the medium; and
a controller configured to operate the imaging device and the driver in cooperation to capture the interior image while creating the shear wave when the imaging device is placed for use to capture the interior image.

3. The apparatus of claim 2 wherein the contact surface of the point source forms a partial sphere for contacting the target surface of the medium.

4. The apparatus of claim 2 wherein the contact surface of the point source is radially symmetric about an axis through the contact surface and includes no high frequency spatial components.

5. The apparatus of claim 2 wherein the contact surface of the point source includes a convex surface shaped to provide initial contact with the medium at a single point.

6. The apparatus of claim 2 wherein the contact surface includes a curved shape selected to mitigate high frequency components within the shear wave.

7. The apparatus of claim 2 wherein the driver is configured to drive the contact surface of the point source into the target surface of the medium along an axis substantially normal to the target surface of the medium.

8. The apparatus of claim 2 further comprising two or more point sources.

9. The apparatus of claim 8 wherein the two or more point sources are positioned in line with a line through a linear ultrasound array of the imaging device.

10. The apparatus of claim 8 wherein the two or more point sources are positioned transverse to a line through a linear ultrasound array of the imaging device.

11. The apparatus of claim 8 wherein the controller is configured to operate the two or more point sources to steer the shear wave toward a region of interest within the medium.

12. The apparatus of claim 2 wherein the imaging device includes a linear ultrasound array, the apparatus further comprising a second contact surface of the linear ultrasound array for placing in contact with the target surface of the medium,
wherein the strain relief is configured to extend from the imaging device and define a line between a second location where the strain relief contacts the target surface of the medium when the imaging device is placed for use and a third location on the second contact surface of the linear ultrasound array, wherein an extremity of the point source is offset from the line away from the medium when the imaging device is placed for use and the driver is prepared to mechanically drive the point source of mechanical energy into the target surface of the medium to create the shear wave.

13. The apparatus of claim 2 wherein the driver includes a voice coil actuator to linearly drive the point source toward the target surface of the medium.

14. The apparatus of claim 2 wherein the driver includes a Hall effect sensor configured to detect a position of the point source.

15. The apparatus of claim 2 wherein the driver includes a free floating cylindrical magnet positioned within a conductive coil and controllable by a current through the conductive coil to accelerate toward the target surface of the medium and impact a stop within the conductive coil to deliver kinetic energy through the point source and create the shear wave.

16. The apparatus of claim 2 wherein the imaging device is a linear ultrasound array.

17. The apparatus of claim 2 wherein the imaging device captures a plurality of images of a transverse plane through the medium using acoustic energy that propagates through the medium at least one order of magnitude more quickly than the shear wave generated by the driver and the point source.

18. The apparatus of claim 2 wherein the point source is positioned relative to the imaging device so that the point source has the offset from the target surface of the medium when the imaging device is placed for use against the target surface of the medium, and wherein the driver is configured to drive the point source through the offset into contact with the target surface in order to strike the target surface and create the shear wave.

* * * * *